(12) United States Patent
Yoshioka et al.

(10) Patent No.: US 9,693,996 B1
(45) Date of Patent: Jul. 4, 2017

(54) CHLOROPHYLL C CONTAINING DEGRANULATION SUPPRESSOR

(71) Applicant: MARUHA NICHIRO CORPORATION, Tokyo (JP)

(72) Inventors: Hisashi Yoshioka, Kumamoto (JP); Akira Kamata, Ibaraki (JP); Tatsuya Konishi, Ibaraki (JP); Hiroshi Oda, Ibaraki (JP); Tadakazu Tamai, Tokyo (JP)

(73) Assignee: MARUHA NICHIRO CORPORATION, Tokyo (JP)

( * ) Notice: Subject to any disclaimer, the term of this patent is extended or adjusted under 35 U.S.C. 154(b) by 0 days.

(21) Appl. No.: 15/452,376

(22) Filed: Mar. 7, 2017

Related U.S. Application Data (62) Division of application No. 14/367,638, filed as application No. PCT/JP2012/084114 on Dec. 28, 2012.

(30) Foreign Application Priority Data

Dec. 28, 2011 (JP) ................................. 2011-288085

(51) Int. Cl.
| | | |
|---|---|---|
| A61K 31/40 | (2006.01) |
| A61K 31/409 | (2006.01) |
| A61K 36/03 | (2006.01) |
| A61K 31/7008 | (2006.01) |
| A61K 31/737 | (2006.01) |

(52) U.S. Cl.
CPC ............ *A61K 31/409* (2013.01); *A61K 31/40* (2013.01); *A61K 31/7008* (2013.01); *A61K 31/737* (2013.01); *A61K 36/03* (2013.01)

(58) Field of Classification Search
CPC ............................ A61K 31/40; A61K 31/409
See application file for complete search history.

(56) References Cited

U.S. PATENT DOCUMENTS

| 5,508,033 A | 4/1996 | Briand |
| 5,661,017 A | 8/1997 | Dunahay et al. |
| 2003/0096027 A1 | 5/2003 | Babish et al. |
| 2006/0134127 A1 | 6/2006 | Okamoto et al. |

FOREIGN PATENT DOCUMENTS

| EP | 1 142 985 A1 | 10/2001 |
| EP | 1 555 028 A1 | 7/2005 |
| JP | 10-72362 A | 3/1998 |
| JP | 11-21247 A | 1/1999 |
| JP | 2000-175680 A | 6/2000 |
| JP | 2003-321474 A | 11/2003 |
| JP | 2006-22002 A | 1/2006 |
| JP | 4012977 B2 | 11/2007 |
| JP | 4212838 B2 | 1/2009 |
| JP | 2010-70531 A | 4/2010 |
| JP | 2011-68680 A | 4/2011 |
| WO | WO 2004/019971 A1 | 3/2004 |
| WO | WO 2008/010335 A1 | 1/2008 |

OTHER PUBLICATIONS

Barnhill et al., "Chondroitin Product Selection for the Glucosamine/Chondroitin Arthritis Intervention Trial", Journal of the American Pharmacists Association, Jan./Feb. 2006, vol. 46, No. 1, pp. 14-24.
Bruyere et al., "Glucosamine and Chondroitin Sulfate as Therapeutic Agents for Knee and Hip Osteoarthritis", Drugs Aging, 2007, vol. 24. No. 7, pp. 573-580.
Chernomorsky et al., "Review Article: Biological Activities of Chlorophyll Derivatives", New Jersey Medicine, Aug. 1988, vol. 85, No. 8, pp. 669-673.
Chlorophyll-Structures, Reactions, Functions—, 2011, pp. 69-70.
Clegg et al., "Glucosamine, Chondroitin Sulfate, and the Two in Combination for Painful Knee Osteoarthritis", The New England Journal of Medicine, Feb. 23, 2006, vol. 354, No. 8, pp. 795-808.
International Search Report, issued in PCT/JP2012/084114, dated Mar. 19, 2013.
Leeb et al., "A Metaanalysis of Chondroitin Sulfate in the Treatment of Osteoarthritis", The Journal of Rheumatololy, vol. 27, 2000, pp. 205-211.
Mazieres et al., "Chondroitin Sulfate in Osteoarthritis of the Knee: A Prospective, Double Blind, Placebo Controlled Multicenter Clinical Study", The Journal of Rheumatology, vol. 28, 2001, pp. 173-181.
Miller et al., "Discovery of a free-living chlorophyll d-producing cyanobacterium with a hybrid proteobacterial/cyanobacterial small-subunit rRNA gene", PNAS, Jan. 18, 2005, vol. 102, No. 3, pp. 850-855.
Mizoguchi et al., "Stereochemical determination of the unique acrylate moiety at the 17-position in chlorophylls-c from a diatom Chaetoseros calcitrans and its effect upon electronic absorption properties", Organic & Biomolecular Chemistry, 2009, vol. 7, No. 10, pp. 2120-2126.
Morreale et al., "Comparison of the Antiinflammatory Efficacy of Chondroitin Sulfate and Diclofenac Sodium in Patients with Knee Osteoarthritis", The Journal of Rheumatology, vol. 23, 1996, pp. 1385-1391.
Researches in Organic Geochemistry, vol. 22, 2007. pp. 43-55.
Sakai et al., "Inhibition of Mast Cell Degranulation by Phycoerythrin and its Pigment Moiety Phycoerythrobilin, Prepared from Porphyra yezoensis", Food Science and Technology Research, 2011, vol. 17, No. 2, pp. 171-177.
Sakai et al., "Effect of glucosamine and related compounds on the degranulation of mast cells and ear swelling induced by dinitrofluorobenzene in mice", Life Sciences 86(9-10), 2010, pp. 337-343.
Yoshioka et al., "Inhibitory effect of chlorophyll c2 from brown algae, Sargassum horneri, on degranulation of RBL-2H3 cells", Journal of Functional Foods, 2013, vol. 5, No. 1, pp. 204-210, CODEN: JFFOAX, ISSN: 1756-4646.

(Continued)

*Primary Examiner* — Yong Chong
(74) *Attorney, Agent, or Firm* — Birch, Stewart, Kolasch & Birch, LLP (57) ABSTRACT

Degranulation suppressors are provided that are effective against allergic disease and osteoarthritis. The degranulation suppressors contain chlorophyll c.

4 Claims, 6 Drawing Sheets

(56) References Cited

OTHER PUBLICATIONS

Extended European Search Report dated Dec. 8, 2015, for European Application No. 12861764.4.
Hirota et al,. "Studies On Chlorophyll of Marine Algae 3, Chlorophyll C of Brown Seaweed," Database Biosis Biosciences Information Service, XP-002749443, Database Accession No. PREV198171019781, vol. 46, No. 7, 1980, pp. 1-2.
Wilhelm, "Purification and identification of chlorophyll $c_1$ from the green alga Mantoniella squamata," Biochimica et Biophysica Acta, vol. 892, 1987, pp. 23-29.
Jeffrey, S.W., "Preparation and Some Properties of Crystalline Chlorophyll C1 and C2 From Marine Algae," Biochemica et Biophysica Acta, 1972, vol. 279, pp. 15-33.
Myers, S.P. et al, "A combined phase I and II open label study on the effects of a seaweed extract nutrient complex on osteoarthritis," Biologics: Targets & Therapy, 2010, vol. 4, pp. 33-44.
Sugiura , Y. et al, "Inhibitory effects of seaweeds on histamine release from rat basophile leukemia cells (RBL-2H3)," Fisheries Science, 2006, vol. 72, pp. 1286-1291.

① Control group
② Test group fed 1.0 wt% of the dry powder of the brown alga *hormeri* (Turner) *C. Agardh* as a concentrated form of chlorophyll c
③ Test group fed 3.0 wt% of the dry powder of the brown alga *hormeri* (Turner) *C. Agardh* as a concentrated form of chlorophyll c
④ Test group fed 1.1 wt% of the 80% hydrous ethanol extract of the brown alga *hormeri* (Turner) *C. Agardh* as a highly concentrated form of chlorophyll c

FIG. 11

① Control group
② Drug administered group
③ Test group fed 2.0 wt% of the dry powder of the brown alga *hormeri* (Turner) *C. Agardh* as a concentrated form of chlorophyll c
④ Test group fed 0.2 wt% of the 80% hydrous ethanol extract of the brown alga *hormeri* (Turner) *C. Agardh* as a highly concentrated form of chlorophyll c
⑤ Test group fed 1.0 wt% of the 80% hydrous ethanol extract of the brown alga *hormeri* (Turner) *C. Agardh* as a highly concentrated form of chlorophyll c

FIG. 12

CHLOROPHYLL C CONTAINING DEGRANULATION SUPPRESSOR

This application is a Division of U.S. patent application Ser. No. 14/367,638 filed on Jun. 20, 2014, which is the National Phase of PCT/JP2012/084114 filed Dec. 28, 2012, which claims priority under 35 U.S.C. §119(a) to Patent Application No. 2011-288085 filed in Japan on Dec. 28, 2011, all of which are hereby expressly incorporated by reference into the present application.

TECHNICAL FIELD

The present invention relates to degranulation suppressors containing chlorophyll c.

BACKGROUND ART

In recent years, as the eating habit of Japanese people has changed and as air pollution and infections have decreased, the incidences of various allergic diseases typified by pollinosis, food allergy, atopic dermatitis, bronchial asthma and contact hypersensitivity are increasing rapidly, and so are the numbers of patients suffering from osteoarthritis and other bone/joint related diseases as aging accelerates in the Japanese society.

According to the 2003 Survey of Health and Welfare compiled by the Ministry of Health, Labor and Welfare (MHLW), more than forty million people accounting for about a third (35.9%) of Japan's population, irrespective of sex and age, present with allergic symptoms in either the skin, respiratory organs, or the eye and nose.

Data by disease can be found in the 2010 Report of Akazawa Group in Scientific Research under MHLW grant; in the 2005-2008 period, the prevalence of infantile bronchial asthma was 13.8% at ages 6-7, 9.5% at ages 13-14, and 8.3% at ages 16~18 whereas the prevalence of bronchial asthma in adults (aged 20-44) was 5.4%. As regards allergic rhinitis and pollinosis, the 2009 Clinical Guideline for Nasal Allergy reports that in the 1998-2008 period, the overall prevalence of allergic rhinitis increased from 29.8% to 39.4% and that of Japanese cedar pollinosis increased from 16.2% to 26.5%. Speaking of atopic dermatitis, its prevalence was 13.2% at age 3, 10.6% in sixth graders at elementary school, 9.4% in the twenties, 8.3% in the thirties, 4.8% in the forties, and 2.5% in the fifties to sixties (the 2008 Clinical Guideline for Atopic Dermatitis).

Allergic diseases occurring in the daily life of Japanese people are one of the major factors that lower their quality of life (QOL). According to the 2003 MHLW Survey, idem, approximately a half (53.4%) of patients complaining of allergic symptoms in respiratory organs responded that they "could not sleep well" and approximately 40% (37.2%) of patients suffering allergic symptoms in the eye and nose responded that they "could not concentrate on work, housekeeping, or schoolwork."

Conventional treatments of allergic diseases have involved medication of drugs such as antihistamines and steroids as part of symptomatic therapy but a problem with these drugs is that they cause serious side effects if administered for an extended period of time. It has, therefore, been desired to develop an ingredient that can be manufactured in a safe and easy way and which is capable of alleviating, suppressing or preventing allergic symptoms, with the additional feature that it can be integrated into the daily dietary life.

As aging accelerates in the Japanese society, bone/joint diseases such as osteoarthritis and osteoporosis are also increasing in number year by year. According to the 2007 National Livelihood Survey compiled by MHLW, two major causes for needed care were joint disease and fracture/falling which accounted for 20.2% (ranking first) and 12.5% (ranking fourth), respectively, of the persons in need of support, whereas they accounted for 9.4% (ranking fourth) and 8.4% (ranking fifth), respectively, of the persons in need of nursing care; thus, bone/joint diseases are one of the major factors that degrade the activities of daily living (ADL) and QOL of Japanese people. In 2007, the Japanese Orthopaedic Association proposed a concept called "locomotive syndrome" which refers to either a state that requires nursing care or one presenting a high risk for the need of nursing care, both due to a locomotor disability and in 2009, Yoshimura et al. at the University of Tokyo Hospital conducted a large-scale resident's cohort study called Research on Osteoarthritis/Osteoporosis Against Disability (ROAD) and reported that as many as forty-seven million people (aged 40 and above) were found to have a locomotive syndrome. Obviously, there exists an urgent need to cope with allergic disease and bone/joint disease because, for one thing, they are quite serious diseases that can potentially degrade ADL and QOL as well as shortening the health span and, for another thing, the ever-growing medical costs must be reduced.

Under these circumstances, active efforts are being made to develop pharmaceutical drugs and food ingredients that can alleviate, suppress or prevent allergic disease and osteoarthritis. Food ingredients so far reported to have an allergy suppressing action include, for example, *Lactobacillus* (Patent Document 1), royal jelly (Patent Document 2), fucoidan which is a water-soluble polysaccharide component in seaweeds (Patent Documents 3 and 4), and alginic acid (Patent Document 5).

It is known that the degranulation reaction of mast cells or basophiles is critical to the onset of various allergic diseases including pollinosis, atopic dermatitis, allergic rhinitis, and allergic conjunctivitis. When an allergen invades the body, the production of an allergen-specific antibody is induced and the allergen-specific antibody produced binds to the surface of a cell such as a mast cell or a basophile, whereupon sensitization is established. When the body is invaded again by an allergen, it binds the allergen-specific antibody on the surface of the mast cell or basophile, whereupon a granule containing a chemical mediator is released out of the cell, triggering an allergic reaction such as enhancement of vascular permeability or constriction of bronchial smooth muscle. Hence, one effective way to suppress various allergic diseases including pollinosis, atopic dermatitis, allergic rhinitis, and allergic conjunctivitis is by suppressing this degranulation reaction.

Food ingredients so far reported to have the degranulation suppressing action include, for example, a plant (galena) extract (Patent Document 6) and phycoerythrin found in red algae (Non-Patent Document 1).

Furthermore, a recent study reported that a glucosamine hydrochloride having an osteoarthritis suppressing action exerted a degranulation suppressing action and also reported was an osteoarthritis suppressing effect mediated by the degranulation suppressing action (Non-Patent Document 2). These results suggest that by investigating the degranulation suppressing action, not only the effect for suppressing allergic disease but also the effect for suppressing osteoarthritis can be verified.

Aside from the glucosamine hydrochloride, various other ingredients have been reported to have the osteoarthritis suppressing action and they include a chondroitin sulfate (Non-Patent Documents 3, 4, 5, 6, 7 and 8) and plant extracts such as those of a plant of the family Compositae (Patent Document No. 7) and spices (Patent Document 8).

Chlorophyll which is a photosynthesis pigment typically contained in plants may be defined as a metal complex of cyclic tetrapyrrole coordinated with Mg or Zn and while it is primarily used as a colorant and food additives that take advantage of its nature as pigment, chlorophyll's recent medical application in photodynamic therapy (PDT) is worth mention (Non-Patent Document 9). In this connection, chlorophyll of high purity is extracted from plants, algae, etc. using organic solvents, etc. and is subsequently separated and purified using an absorption photometer, high-performance liquid chromatography, etc. (Non-Patent Documents 10, 11, and 12). Concerning chlorophyll's functionality, a report was made of a chlorophyllin copper complex as a chlorophyll analog having an antioxidization-based antimicrobial, anticancer, antiatherosclerotic, antipsoriatic and other beneficiary actions (Non-Patent Document 13); however, no report has yet been published about the degranulation suppressing effect of chlorophyll that contributes to allergy suppression as by suppressing vascular permeability or to osteroarthritis suppression.

CITATION LIST

Patent Literature

Patent Document 1: Japanese Patent No. 4212838
Patent Document 2: WO2004/019971 A1
Patent Document 3: JP Hei 11-21247 A
Patent Document 4: JP Hei 10-72362 A
Patent Document 5: Japanese Patent No. 4012977
Patent Document 6: JP Hei 2010-70531 A
Patent Document 7: WO2008/010335
Patent Document 8: JP Hei 2006-22002 A Non-Patent Literature Non-Patent Document 1: Food science and technology research. Vol. 17, No. 2, 171-177 (2011)
Non-Patent Document 2: Life science. 86(9-10), 337-343 (2010)
Non-Patent Document 3: The journal of Rheumatology. 27, 205-211 (2000)
Non-Patent Document 4: The journal of Rheumatology. 23, 1385-1391 (1996)
Non-Patent Document 5: The journal of Rheumatology. 28, 173-181 (2001)
Non-Patent Document 6: The new ENGLAND journal of medicine. 354, No. 8, 795-808 (2006)
Non-Patent Document 7: Journal of the American pharmacists association. Vol. 46, No. 1, 14-24 (2006)
Non-Patent Document 8: Drug aging. 24(7), 573-580 (2007)
Non-Patent Document 9: Chlorophyll—Structures, Reactions, Functions—; pp. 69-70 (2011)
Non-Patent Document 10: Researches in Organic Geochemistry. 22, pp. 43-55 (2007)
Non-Patent Document 11: PNAS. Vol. 102, pp. 850-855 (2005)
Non-Patent Document 12: Organic & Biomolecular Chemistry. Vol. 7, No. 10, pp. 1989-2224 (2009)
Non-Patent Document 13: New jersey medicine. 85(8), 669-673 (1988)

SUMMARY OF INVENTION

Technical Problem

The problem the present invention addresses is the recent rapid increase in the number of patients with allergic disease and bone/joint disease about which something must be done as soon as possible; to reduce the incidence of these diseases, the present invention provides degranulation suppressing agents that contain chlorophyll c as an active ingredient that shows a degranulation suppressing action.

Solution to Problem

As a result of intensive studies, the present inventors found that while there are a lot of chlorophylls available, chlorophyll c or an algal powder or an algal extract that contain chlorophyll c as an ingredient involved in activity has a degranulation suppressing action, and this finding has led to the accomplishment of the present invention. Briefly, the present invention has as its objective providing chlorophyll c or a composition for alleviating, treating or preventing allergic disease or osteoarthritis by suppressing the degranulation reaction of mast cells, basophiles, etc., said composition being characterized by comprising chlorophyll c as an active ingredient.

Briefly, the present invention relates to a degranulation suppressing composition comprising chlorophyll c. This degranulation suppressing composition may be used as an osteroarthritis suppressing agent or an allergy suppressing agent. It may also be used as a food in which chlorophyll c has been incorporated. Specifically, it may be used as a degranulation suppressing, functional food comprising chlorophyll c. It may also be used as a feed or pet food in which chlorophyll c has been incorporated. Specifically, it may be used as a degranulation suppressing feed or pet food in which chlorophyll c has been incorporated.

Advantageous Effects of Invention

According to the present invention, by using chlorophyll c or an extract of a particular kind of seaweeds that contain chlorophyll c, there can be obtained a degranulation suppressor that can be taken orally and which comprises chlorophyll c as an active ingredient; use can be made of the suppressor as a pharmaceutical, a food or beverage, a feed or a pet food. By orally taking such pharmaceutical, food or beverage, feed or pet food, the degranulation reaction of mast cells or basophiles can be suppressed to enable alleviation, suppression or prevention of allergic disease or osteoarthritis.

DESCRIPTION OF EMBODIMENTS

As noted above, the present invention relates to degranulation suppressor compositions comprising chlorophyll c and it will be descried below in greater details.

Chlorophyll c is a porphyrin compound contained in certain algae whose names are mentioned below; it has the structural formula:

[Formula 1]

chlorophyll c1 ($R^7$:$CH_3$, $R^8$:$CH_2CH_3$)
chlorophyll c2 ($R^7$:$CH_3$, $R^8$:$CH=CH_2$)
chlorophyll c3 ($R^7$:$COOCH_3$, $R^8$:$CH=CH_2$)

and consists of three species c1, c2 and c3. The structures of chlorophylls c1, c2 and c3 are, unlike molecules having the chlorin 7C skeleton such as chlorophylls a, b and d which are incapable of suppressing the degranulation reaction, characterized by having the porphyrin 7C skeleton with a C17-C18 double bond as depicted in the above structural formula. Their molecular weights are close to each other—c1 (610), c2 (608) and c3 (653)—and so are the spectra for absorbance *maxima* in diethyl ether—c1 (444.4 nm), c2 (447.8 nm) and c3 (450.8 nm). Either form of chlorophyll c starts to be biosynthesized in algae from divinyl protochlorophyllide a and exhibits a photosynthetic action and an antioxidizing action.

It is through the suppression of the degranulation from mast cells or basophiles that chlorophyll c is capable of alleviating, suppressing and preventing allergic disease or osteoarthritis.

The starting materials from which the chlorophyll c to be contained in the composition of the present invention can be obtained are not particularly limited. Chlorophyll c which is one of the photosynthetic pigments found in plants is known to be contained in oxygen-producing photosynthetic organisms, particularly of the Division Dinoflagellata, the Division Cryptophyta, the Division Heterokontophyta including the Class Chrysophyceae, the Class Raphidophyceae, the Class Phaeophyceae, the Class Bacillariophyceae (Diatomea) and the Class Eustigmatophyceae, as well as the Division Haptophyta. Preferred examples are brown algae of: the order ECTOCARPALES Setchell et Gardner, 1922, the family Ectocarpaceae C. Agardh, 1828, the genus *Acinetospora* Bornet, 1892 [*Ectocarpus filamentosus, Ectocarpus ugoensis*], the genus *Asteronema* Delepine et Asensi, 1975 nom. cons. [*breviarticulatum* (J. Agardh) Ouriques et Bouzon, *Ectocarpus breviarticulatus, Feldmannia breviarticulata, Hincksia breviarticulata*], the genus *Ectocarpus* Lyngbye, 1819 nom. cons. [*arctus* Kuetzing, *confervoides, fusiformis* Nagai, *laurenciae* Yamada, *siliculosus* (Dillwyn) Lyngbye, *socialis* Setchell et Gardner, *yezoensis* Yamada et Tanaka], the genus *Feldmannia* Hamel, 1939 [*formosana* (Yamada) Itono, *Ectocarpus formosanus, irregularis* (Kuetzing) Hamel, *Ectocarpus irregularis, Ectocarpus izuensis*], the genus *Hincksia* J. E. Gray, 1864 [*granulosa* (J. E. Smith) Silva, *Ectocarpus granulosus, Giffordia granulosa, indica* (Sonder) J. Tanaka, *Ectocarpus indicus, Feldmannia indica, Giffordia indica, mitchellae* (Harvey) Silva, *Ectocarpus mitchellae, Giffordia mitchellae, Ectocarpus ovatus, Giffordia ovata, Ectocarpus sandrianus, Giffordia sandriana*], the genus *Laminariocolax* Kylin, 1947 [*aecidioides* (Rosenvinge) Peters, *Gononema aecidioides, Streblonema aecidioides*], the genus *Laminarionema* Kawai et Tokuyama, the genus *Spongonema* Kuetzing, 1849 [*tomentosum* (Hudson) Kuetzing], the genus *Streblonema* Derbes et Solier in Castagne, 1851 [*evagatum* Setchell et Gardner, *fasciculatum* Thuret], the family Pylaiellaceae Pedersen, 1984, the genus *Bachelotia* (Bornet) Kuckuck ex Hamel, 1939 [*antillarum* (Grunow) Gerloff], the genus *Pylaiella* Bory, 1823 orth. cons. [*littoralis* (Linnaeus) Kjellman], the family Sorocarpaceae Pedersen, 1977, the genus *Botrytella* Bory, 1822 [*parva* (Takamatsu) Kim, *micromora, Sorocarpus uvaeformis*], the genus *Polytretus* Sauvageau, 1900 [*reinboldii* (Reinke) Sauvageau, *Ectocarpus intricatus, Ectocarpus iwadatensis, Ectocarpus recurvatus*]; the order RALFSIALES Nakamura, 1972 emend. Lin et Kawai (61), the family Lithodermataceae Hauck, 1883, the genus *Pseudolithoderma* Svedelius in Engler et Prantl, 1911 [*subextensum* (Waern) S. Lund], the family Ralfsciaceae Fardlow, 1881, the genus *Analipus* Kjellman, 1889 [*filiformis* (Ruprecht) Papenfuss, *gunjii* (Yendo) Kogame et Yoshida, *Chordaria gunjii, japonicus* (Harvey) Wynne, *Heterochordaria abietina*], the genus *Diplura* Hollenberg, 1969 [*simplex*

J. Tanaka et Chilhara], the genus *Endoplura* Hollenberg, 1969 [*aurea* Hollenberg], the genus *Hapalospongidion* Saunders, 1899 [*schmidtii* (Weber-van Bosse) Silva, *Mesospora schmidtii*], the genus *Heteroralfsia* Kawai, 1989 [*saxicola* (Okamura et Yamada) Kawai, *Gobia saxicola*, *Saundersella saxicola*], the genus *Ralfsia* Berkeley in Smith et Sowerby, 1843 [*fungiformis* (Gunnerus) Setchell et Gardner, *verrucosa* (Areschoug) Areschoug]; the order SYRINGODERMATALES Henry, 1984, the family Synringodermataceae Henry, 1084, the genus *Syringoderma* Levring, 1940 [*abyssicola* (Setchell et Gardner) Levring]; the order SPHACELARIALES Migula 1909, the family Sphacelariaceae Decaisne, 1842, the genus *Sphacelaria* Lyngbye in Hornemann, 1818 [*californica* Sauvageau, *cornuta* Sauvageau, *divaricata* Montagne, *furcigera* sensu Reinke, *hizikiae*, *prostrata*, *radicans* sensu Yendo, *tenuis*, *nipponica* Kitayama, *plumigera* Holmes ex Hauck, *rigidula* Kuetzing, *apicalis*, *caespitosa*, *expansa*, *furcigera*, *iridaeophytica*, *iwagasakensis*, *linearis*, *sessilis*, *subfusca*, *variabilis*, *solitaria* (Pringsheim) Kylin, *divaricata*, *f. japonica*, *shiiyaensis*, *viridis*, *tribuloides* Meneghini, *yamadae* Segawa, *pyriformis*, *radiata*], the family Stypocaulaceae Oltmanns, 1922, the genus *Halopteris* Kuetzing, 1843 [*filicina* (Grateloup) Kuetzing], the genus *Stypocaulon* Kuetzing, 1843 [*durum* (Ruprecht) Okamura]; the order DICTYOTALES Kjellman in Engler et Prantl, 1896, the family Dictyotaceae Lamouroux ex Dumortier, 1822, the genus *Dictyopteris* Lamouroux, 1809 nom. cons. [*divaricata* (Okamura) Okamura, *fucoides* Tanaka, *latiuscula* (Okamura) Okamura, *papenfussii* Tanaka, *plagiogramma* (Montagne) Vickers, *polypodioides* (De Candolle) Lamouroux, *membranacea*, *prolifera* (Okamura) Okamura, *punctata* Noda, *repens* (Okamura) Boergesen, *undulata* Holmes], the genus *Dictyota* Lamouroux, 1809 nom. cons. [*bartayresii* Lamouroux, *dentata* Lamouroux, *dichotoma* (Hudson) Lamouroux, *dilatata* Yamada, *divaricata* Lamouroux, *friabilis* Setchell, *linearis* (C. Agardh) Greville, *maxima* Zanardini, *patens* J. Agardh, *spathulata* Yamada, *spinulosa* Harvey], the genus *Distromium* Levring, 1940 [*decumbens* (Okamura) Levring, *Chlanidophora repens*, *Chlanidote decumbens*], the genus *Homoeostrichus* J. Agardh, 1894 [*flabellatus* Okamura], the genus *Lobophora* J. Agardh, 1894 [*variegata* (Lamouroux) Womersley ex Oliveira, *Gymnosorus collaris*, *Pocockiella variegata*], the genus *Pachydictyon* J. Agardh, 1984 [*coriaceum* (Holmes) Okamura], the genus *Padina* Adanson, 1763 nom. cons. [*arborescens* Holmes, *australis* Hauck, *boryana* Thivy, *crassa* Yamada, *fasciata* Ni-Ni-Win, Arai et Kawai, *japonica* Yamada, *melemele* Abbot et Magruder, *minor* Yamada, *moffittiana* Abbot et Huisman, *okinwaensis* Ni-Ni-Win, Arai et Kawai, *ryukyuana* Y. P. Lee et Kamura, *stipitata* Tanaka et Nozawa, *terricolor* Ni-Ni-Win, Arai et Kawai, *undulata* Ni-Ni-Win, Arai et Kawai], the genus *Ruglopteryx* DeClerk et Coppjans 2009 [*okamurae* (Dawson) Hwang, Lee et Kim in Hwang et al., *Dilophus okamurae*, *Dilophus marginatus*], the genus *Spatoglossum* Kuetzing, 1843 [*crassum* J. Tanaka, *variabile* sensu Yendo, *latum* J. Tanaka, *pacificum* Yendo, *cornigerum* sensu Yendo, *solieri* sensu Yendo], the genus *Stypopodium* Kuetzing, 1843 [*zonale* (Lamouroux) Papenfuss, *lobatum*], the genus *Zonaria* C. Agardh, 1817 nom. cons. [*diesingiana* J. Agardh, *stipitata* Tanaka et K. Nozawa]; the order CHORDARIALES Setchell et Gardner, 1925, the family Acrotrichaceae Kuckuck, 1929, the genus *Acrothrix* Kylin, 1907 [*gracilis* Kylin, *pacifica* Okamura et Yamada], the family Chordariaceae Greville, 1830, the genus *Chordaria* C. Agardh, 1817 nom. cons. [*chordaeformis* (Kjellman) Kawai et Kim, *flagelliformis* (O. F. Mueller) C. Agardh, *gracilis* Setchell et Gardner], the genus *Cladosiphon* Kuetzing, 1843 [*Okamuranus* Tokida, *Eudesme virescens* sensu Okamura, *umezakii* Ajisaka], the genus *Eudesme* J. Agardh, 1882 [*virescens* (Carmichael ex Berkeley) J. Agardh], the genus *Heterosaundersella* Tokida, 1942 [*hattoriana* Tokida], the genus *Myriogloea* Kuckuck ex Oltamanns, 1922 [*simplex* (Segawa et Ohta) Inagaki], the genus *Papenfussiella* Kylin, 1940 [*kuromo* (Yendo) Inagaki, *Myriocladia kuromo*], the genus *Saundersella* Kylin, 1940 [*simplex* (Saunders) Kylin, *Gobia simplex*], the genus *Sauvageaugloia* Hamel ex Kylin, 1940 [*ikomae* (Narita) Inagaki], the genus *Sphaerotrichia* Kylin, 1940 [*divaricata* (C. Agardh) Kylin, *japonica*, *sadoensis*, *Castagnea divaricata*, *Chordaria cladosiphon*, *firma* (E. Gepp) Zinova (20), *Chordaria firma*], the genus *Tinocladia* Kylin, 1940 [*crassa* (Suringar) Kylin, *Eudesme crassa*], the family Elachistaceae Kjellman, 1890, the genus *Elachista* Duby, 1830 nom. et orth. cons. [*coccophorae* Takamatsu, *orbicularis*, *Gonodia orbicularis*, Okamura Yoshida, *fucicola* sensu Okamura, *globosa* Takamatsu, *taeniaeformis* Yamada, *crassa*, *flaccida* auct. Japon., *sadoensis*, *tenuis* Yamada, *vellosa* Takamatsu], the genus *Halothrix* Reinke, 1888 [*ambigua* Yamada, *lumbricalis* sensu Takamatsu, *tortuosa*], the genus *Leptonematella* Silva, 1959 [*fasciculata* (Reinke) Silva], the family Leathesiaceae Farlow, 1881, the genus *Kurogiella* Kawai, 1993 [*saxicola* Kawai], the genus *Leathesia* S. F. Gray, 1821 [*crassipilosa* Takamatsu, *difformis* (Linnaeus) Areschoug, *monilicellulata* Takamatsu, *primaria* Takamatsu, *pulvinata* Takamatsu, *sadoensis* Inagaki, *saxicola* Takamatsu, *granulosa*], the genus *Phaeophysema* Tanaka, Uwai et Kawai 2010 [*pulvinata* (Takamatsu) Tanaka, Uwai et Kawai, *sphaerocephala* (Yamada) Tanaka, Uwai et Kawai], the genus *Vimineolaethesia* Tanaka, Uwai et Kawai [*japonicaa* (Inagaki) Tanaka, Uwai et Kawai], the genus *Myriactula* Kuntze, 1898 [*sargassi* (Yendo) Feldmann, *saromaensis* Yamada et Iwamoto], the family Petrospongiaceae Recault in Recault et al. 2009, the genus *Petrospongium* Naegeli ex Kuetzing, 1858 [*rugosum* (Okamura) Setchell et Gardner, *Cylindrocarpus rugosus*], the family Myrionemataceae Naegeli, 1847, the genus *Compsonema* Kuckuck, 1899 [*nummuloides* Setchell et Gardner], the genus *Hecatonema* Sauvageau [*maculans* (Collins) Sauvageau, *terminale* (Kuetzing) Kylin], the genus *Microspongium* Reinke, 1888 [*Myrionema globosum*], the genus *Myrionema* Greville, 1827 [*corunnae* Sauvageau], the genus *Protectocarpus* Kuckuck et Kommann, 1955 [*speciosus* (Boergesen) Kuckuck ex Kommann, *Compsonema ramulosum* sensu Noda], the family Spermatochnaceae Kjellman, 1890, the genus *Nemacystus* Derbes et Solier, 1850 [*decipiens* (Suringar) Kuckuck], the genus *Stilophora* J. Agardh, 1841 nom. cons. [*tenella* (Esper) Silva, *rhizodes*]; the order DICTYOSIPHONALES Setchell et Gardner, 1925, the family Asperococcaceae Farlow, 1881, the genus *Asperococcus* Lamouroux, 1813 [*bullosus* Lamouroux, *turneri*], the genus *Melanosiphon* Wynne, 1969 [*intestinalis* (Saunders) Wynne, *Myelophycus intestinalis*], the family Coilodesmaceae Setchell et Gardner, 1925, the genus *Coilodesme* Stroemfelt, 1886 [*cystoseirae* (Ruprecht) Setchell et Gardner, *japonica* Yamada, *cystoseirae* sensu Yendo], the family Delamareaceae A. D. Zinova, 1953, the genus *Delamarea* Hariot, 1889 [*attenuata* (Kjellman) Rosenvinge], the genus *Stschapovia* A. D. Zinova, 1954, the family Dictyosiphonaceae Kuetzving, 1849, the genus *Dictyosiphon* Greville, 1830 nom. cons. [*chordaria* Areschoug, *foeniculaceus* (Hudson) Greville, *hippuroides*], the family Punctariaceae (Thuret) Kjellman, 1880, the genus *Pogotrichum* Reinke, 1892 [*yezoense* (Yamada et Nakamura) Sakai et Saga, *Litosiphon yezoense*], the genus *Punctaria* Greville, 1830 [*flaccida* Nagai, *kinoshitae* Yamada et Iwamoto, *tenuis*, *latifolia* Greville, *mageshimensis* Tanaka, *occidentalis* Setchell et Gardner, *chartacea* sensu Umezaki, *conglomerata*, *pilosa* Umezaki, *plantaginea* (Roth) Greville, *rubescens* sensu Yendo, *projecta* Yamada], the genus *Trachynema* Pedersen, 1985 [*groenlandicum* (Lund) Pedersen], the family Striariaceae Kjellman, 1890, the genus *Coelocladia* Rosenvinge, 1893 [*arctica* Rosenvinge], the genus *Stictyosiphon* Kuetzing, 1843 [*soriferus* (Reinke) Rosenvinge, *Kjellmania arasakii*], the genus *Striaria* Greville, 1828 [*attenuata* (Greville) Greville]; the order SCYTOSIPHONALES J. Feldmann, 1949, the family Chnoosporaceae Setchell et Gardner, 1925, the genus *Chnoospora* J. Agardh, 1847 [*implexa* J. Agardh, *minima* (Hering) Papenfuss, *pacifica*], the family Scytosiphonaceae Farlow, 1881, the genus *Colpomenia* (Endlicher) Derbes et Solier in Castagne, 1851 [*bullosa* (Saunders) Yamada, *sinuosa* f. *deformans*, *peregrina* (Sauvageau) Hamel, *phaeodactyla* Wynne et J. N. Norris, *sinuosa* (Mertens ex Roth) Derbes et Solier], the genus *Hydroclathrus* Bory, 1825 [*clathratus* (C. Agardh) Howe, *tenuis* Tseng et Lu], the genus *Myelophycus* Kjellman in Engler et Prantl, 1893 [*cavus* J. Tanaka et Chihara, *simplex* (Harvey) Papenfuss, *caespitosus*], the genus *Petalonia* Derbes et Solier, 1850 nom. cons. [*binghamiae* (J. Agardh) Vinogradova, *Endarachne binghamiae*, *fascia* (O. F. Mueller) Kuntze, *Ilea fascia*, *zosterifolia* (Reinke) Kuntze], the genus *Rosenvingea* Boergesen, 1914 [*intricata* (J. Agardh) Boergesen], the genus *Scytosiphon* C. Agardh, 1820 nom. cons. [*canaliculatus* (Setchell et Gardner) Kogame, *gracilis* Kogame, *lomentaria* (Lyngbye) Link, *tenellus* Kogame]; the order CUTLERIALES Oltmanns, 1922, the family Cutleriaceae Hauck, 1883, the genus *Cutleria* Greville, 1830 [*adspersa* (Roth) De Notaris, *cylindrica* Okamura, *multifida* (Turner) Greville]; the order SPOROCHNALES Sauvageau, 1926, the family Sporochanaceae Greville, 1830, the genus *Carpomitra* Kuetzing, 1843 nom. cons. [*costata* (Stackhouse) Batters, *cabrerae*], the genus *Nereia* Zanardini, 1846 [*intricata* Yamada], the genus *Sporochnus* C. Agardh, 1817 [*radiciformis* (R. Brown ex Turner) C. Agardh, *scoparius*]; the order DESMARESTIALES Setchell et Gardner, 1925, the family Desmarestiaceae (*Thuret*) Kjellman, 1880, the genus *Desmarestia* Lamouroux, 1813 nom. cons. [*ligulata* (Stackhouse) Lamouroux, *tabacoides* Okamura, *viridis* (Mueller) Lamouroux]; the order LAMINARIALES Kylin, 1917, the family Akkesiphycaceae Kawai et Sasaki, 2000, the genus *Akkesiphycus* Yamada et Tanaka, 1944 [*lubricus* Yamada et Tanaka], the family Alariaceae Setchell et Gardner, 1925, the genus *Alaria* Greville, 1830 nom. cons. [*angusta* Kjellman, *crassifolia* Kjellman, *paradisea* (Miyabe et Nagai) Widdowson, *Pleuropterum paradiseum*, *praelonga* Kjellman, *taeniata* Kjellman], the genus *Druehlia* Lane et Saunders, 2007 [*fistulosa* (Postels et Ruprecht) Lane et Saunders], the genus *Undaria* Suringar, 1873 [*peterseniana* (Kjellman) Okamura, *pinnatifida* (Harvey) Suringar, *undarioides* (Yendo) Okamura], the family Chordaceae Dumortier, 1822, the genus *Chorda* Stackhouse, 1797 [*asiatica* Sasaki et Kawai, *Chora filum* auct. japon.], the genus *Agarum* Dumortier, 1822 nom. cons. [*clathratum* Dumortier, *cribrosum*, *oharaense* Yamada], the genus *Costaria* Greville, 1830 [*costata* (C. Agardh) Saunders], the family Laminariaceae Bory, 1827, the genus *Ecklonia* Hornemann, 1828 [*cava* Kjellman, *kurome* Okamura, *stolonifera* Okamura], the genus *Eckloniopsis* Okamura, 1927 [*radicosa* (Kjellman) Okamura], the genus *Eisenia* Areschoug, 1876 [*arborea* Areschoug, *bicyclis* (Kjellman) Setchell], the genus *Arthrothamnus* Ruprecht, 1848 [*bifidus* (Gmelin) Ruprecht], the genus *Cymathaere* [*Cymathaere japonica*, *crassifolia* sensu Miyabe et Nagai], the genus *Laminaria* Lamouroux, 1813 nom. cons. [*yezoensis* Miyame], the genus *Saccharina* Stackhouse 1809 [*angustata* (Kjellman) Lane, Mayes, Druehl et Saunders, *Laminaria angustata*, *cichorioides* (Miyabe) Lane, Mayes, Druehl et Saunders, *Laminaria cichorioides*, *coriacea* (Miyabe) Lane, Mayes, Druehl et Saunders, *Laminaria coriacea*, *diabolica* (Miyabe) Lane, Mayes, Druehl et Saunders, *Laminaria diabolica*, *gyrata* (Kjellman) Lane, Mayes, Druehl et Saunders, *Laminaria gyrata*, *Kjellmaniella gyrata*, *japonica* (Areschoug) Lane, Mayes, Druehl et Saunders, *Laminaria japonica*, *kurilensis* Lane, Mayes, Druehl et Saunders, *Cymathaere japonica* Miyabe et Nagai, *latissima* (Linneaus) Lane, Mayes, Druehl et Saunders, *Laminaria saccharina*, *longipedalis* (Okamura) Lane, Mayes, Druehl et Saunders, *Laminaria longipepedalis*, *longissima* (Miyabe) Lane, Mayes, Druehl et Saunders, *Laminaria longissima*, *ochotensis* (Miyabe) Lane, Mayes, Druehl et Saunders, *Laminaria ochotensis*, *religiosa* (Miyabe) Lane, Mayes, Druehl et Saunders, *Laminaria religiosa*, *Sculpera* Lane, Mayes, Druehl et Saunders, *Kjellmaniella crassifolia*, *Saccharina crassifolia*, *yendoana* (Miyabe) Lane, Mayes, Druehl et Saunders, *Laminaria yendoana*], the genus *Streptophyllopsis* Kajimura, 1981 [*kuroshioensis* (Segawa) Kajimura, *Hedophyllum kuroshioense*], the family Pseudochordaceae Kawai et Kurogi, 1985, the genus *Pseudochorda* Yamada, Tokida et Inagaki in Inagaki, 1958 [*gracilis* Kawai et Nabata, *nagaii* (Tokida) Inagaki, *Chordaria nagaii*]; the order ISHIGEALES Cho et Boo in Cho et al., 2004, the family Ishigeaceae Okamura in Segawa, 1935, the genus *Ishige* Yendo, 1907 [*okamurae* Yendo, *sinicola* (Setchell et Gardner) Chihara, *foliacea*]; the order FUCALES Kylin, 1917, the family Fucaceae Adanson, 1763, the genus *Fucus* Linnaeus, 1753 [*distichus* Linnaeus subsp. *evanescens* (C. Agardh) Powell, *evanescens*], the genus *Silvetia* Serrao, Cho, Boo et Brawley in Serrao et al. 1999 [*babingtonii* (Harvey) Serrao et al., *Pelvetia babingtonii*, *Pelvetia wrightii*], the family Sargassaceae Kuetzing, 1843, the genus *Coccophora* Greville, 1830 [*langsdorfii* (Turner) Greville], the genus *Cystoseira* C. Agardh, 1820 nom. cons. [*crassipes* (Mertens ex Turner) C. Agardh, *Cystophyllum crassipes*, *geminata* C. Agardh, *Cystophyllum geminatum*, *hakodatensis* (Yendo) Fensholt, *Cystophyllum hakodatense*], the genus *Hormophysa* Kuetzing, 1843 [*cuneiformis* (Gmelin) Silva, *triquetra*, *Cystoseira prolifera*], the genus *Myagropsis* Kuetzing, 1843 [*myagroides* (Mertens ex Turner) Fensholt, *yendoi*, *Cystophyllum caespitosum*, *Cystophyllum sisymbrioides*, *Cystophyllum turneri*], the genus *Sargassum* C. Agardh, 1820 nom. cons. [*alternato-pinnatum* Yamada, *asymmetricum*, *ammophilum* Yoshida et T. Konno, *araii* Yoshida, *assimile* Harvey, *autumnale* Yoshida, *boreale* Yoshida et Horiguchi, *bulbiferum* Yoshida, *carpophyllum* J. Agardh, *angustifolium* sensu Yamada, *vulgare* var. *linearifolium* sensu Yendo, *confusum* C. Agardh, *crassifolium* J. Agardh, *berberifolium*, *crispifolium* Yamada, *cristaefolium* C. Agardh, *denticarpum* Ajisaka, *duplicatum* Bory, *brevifolium* sensu Yendo, *sandei*, *filicinum* Harvey, *fulvellum* (Turner) C. Agardh, *enerve*, *fusiforme* (Harvey) Setchell, *Hizikia fusiformis*, *giganteifolium* Yamada, *glaucescens* J. Agardh, *hemiphyllum* (Turner) C. Agardh, *hornei* (Turner) C. Agardh, *ilicifolium* (Turner) C. Agardh var. *conduplicatum* Grunow, *incanum* Grunow, *kashiwajimanum* Yendo, *kushimotense* Yendo, *longifructum* Tseng et Lu, *macrocarpum* C. Agardh, *serratifolium* auct. japon., *micracanthum* (Kuetzing) Endlicher, *microceratium* (Mertens ex Turner) C. Agardh, *miyabei* Yendo, *kjellmanianum*, *muticum* (Yendo) Fensholt, *kjellmanianum* f. *muticum*, *myriocystum* J. Agardh, *opacum*, *nigrifolium* Yendo, *nipponicum* Yendo, *okamurae* Yoshida et T. Konno, *pallidum* (Turner) C. Agardh, *patens* C. Agardh, *piluliferum* (Turner) C. Agardh, *pinnatifidum* Harvey, *polycystum* C. Agardh, *polyporum* Monagne, ssp. *ringgoldianum*, ssp. *coreanum* (J. Adardh) Yoshida, *ryukyuense* Shimabukuro et Yoshida, *sagamianum* Yendo, *salicifolioides* Yamada, *hyugaense*, *segii* Yoshida, *racemosum* Yamada et Segi, *ringgoldianum* f. *ellipticum*, *serratifolium* (C. Agardh) C. Agardh, *siliquastrum* (Turner) C. Agardh, *tortile*, *siliquosum* J. Agardh, *spathulophyllum* J. Tanaka, Murakami et Arai, *tenuifolium* Yamada, *thunbergii* (Mertens ex Roth) Kuntze, *tosaense* Yendo, *trichophyllum*

(Kuetzing) Kuntze, *wakayamaense* Yoshida, *yamadae* Yoshida et T. Konno, *Yamamotoi* Yoshida, *yendoi* Okamura et Yamada, *henslowianum* var. *condensatum, yezoense* (*Yamada*) Yoshida et T. Konno, *sagamianum* var. *yezoense*], and the genus *Turbinaria* Lamouroux, 1825 [*conoides* (J. Agardh) Kuetzing, *ornata* (Turner) J. Agardh, *turbinata* (Linnaeus) Kuntze, *trialata*]. Particularly preferred for use as the starting materials for chlorophyll c are *hormeri* (Turner) C. Agardh, *cava* Kjellman, *kurome* Okamura, and kelp (Laminariaceae Bory) which are all brown algae.

The method for obtaining the chlorophyll c to be used in the present invention is not particularly limited if the chlorophyll c is neither decomposed nor denatured. For instance, the starting material to be subjected to extraction may be used as it is or after being subjected to desalting, water-washing and drying processes; alternatively, it may be first reduced to a powder in order to improve the extraction efficiency. If desired, in order to further facilitate the extraction of chlorophyll c out of the cell, a decomposition process may be preliminarily performed by treatment with an enzyme such as protease which degrades such proteins as the one forming the cell membrane or the one binding to chlorophyll c or cellulase which degrades cellulose present in the cell wall and the like. The extract may be concentrated by any suitable technique such as vacuum concentration, freeze concentration or membrane concentration.

The solvent for extracting the chlorophyll c to be used in the present invention is not particularly limited if the chlorophyll c is neither decomposed nor denatured). Examples include water, salt containing aqueous solutions, and organic solvents such as alcohols (e.g. methanol, ethanol and butanol), ethers (e.g. diethyl ether), esters (e.g. ethyl acetate), and ketones (e.g. acetone); preferred examples include ethanol, methanol, acetone, and diethyl ether.

Described below is one specific method for producing chlorophyll c from a chlorophyll c containing alga: for the purpose of concentrating chlorophyll c in a convenient and inexpensive way by removing impurities such as salts, polysaccharides, and other non-chlorophyll c water-soluble and water-insoluble components, the alga is washed under stirring with 1-100 volumes of water and after repeating the same washing operation several times, the alga is dried under appropriate conditions and ground with a mill to produce a dry algal powder as a concentrated form of chlorophyll c.

For the purpose of concentrating chlorophyll c even further, the thus produced dry algal powder as a concentrated form of chlorophyll c may be subjected to extraction with 60%-100%, preferably 80%, hydrous ethanol under stirring overnight at ordinary temperatures. After the extraction, suction filtration is performed to remove the insoluble matter and the resulting extract is rotary evaporated to dryness, thereby yielding an algal hydrous ethanol extract as a concentrated form of chlorophyll c.

For the purpose of concentrating chlorophyll c still further, the thus produced algal hydrous ethanol extract as a concentrated form of chlorophyll c may be subjected to phase separation using n-butanol and water, and the resulting n-butanol fraction may be subjected to further phase separation using hexane and hydrous methanol. The resulting hydrous methanol fraction is fractionated on a silica gel column and an ODS column, eluted on a gradient using an aqueous acetonitrile solution and pure acetonitrile, and fractionated by HPLC involving peak identification based on the absorbance at a wavelength of 254 nm. The resulting fractions and an authentic sample of chlorophyll c were subjected to HPLC and measured for the absorbance at 450 nm; by verifying the occurrence of a peak at the same retention time as for the authentic sample of chlorophyll c, an even more purified form of chlorophyll c can be produced from the starting algal hydrous ethanol extract as a concentrated form of chlorophyll c.

The protease that may be used in the present invention to decompose proteins is not particularly limited. Examples include Newlase F3G, Newlase A, Morushin F, Sumizyme AP, Denapushin 2P, Orientase 20A, Tetoraze S, Brewer's Clarex, Protease YP-SS, Protease A "Amano" G, Protease N "Amano" G, Protease S "Amano" G, Papain W-40, bromelain F, Puromoddo 223LP, Sumizyme LP, Sumizyme FP, Sumizyme LPL, PROTIN SD-NY-10, PROTIN SD-PC-10F, Brewer's Protease, Accelazyme NP50.000, purified Papain, purified Papain for use in foods, Denachimu AP, PTN, Neutrase, nucleicin, Orientase 10NL, Orientase 90N, Orientase ONS, Papain F, trypsin 4.0T, COROLASE N, VERON L10, COROLASE L10, COROLASE 7089, Panchidaze NP-2, Panchidaze P, Aroaze AP-10, Aroaze NP-10, Aroaze NS, Enchiron NBS, Papain, Protex 7L, Protex 14L, Thermoase PC10F, PROTIN SD-AC-10F, PROTIN SD-AY-10, Proleather FG-F, Protease P "Amano" 3G, alkali Protease GL, Protex 6L, Protx 89L, Purafect, Purafect OX, Puroperaze, Protex OXG, Protex 40L, Sumizyme MP, Delvolase, Esperase, Savinase, Alcalase, Clear Lens Pro, Everlase, Kan'nase, Novozyme FM, Biopuraze OP, Biopuraze AL-15FG, Biopuraze 30G, Biopuraze APL-30, Biopuraze XL-416F, Biopuraze SP-20FG, Biopuraze SP-4FG, Protease CL-15, Orientase 22BF, Aroaze XA-10, Enchiron SA, Bakezyme PPU95.000, Bakezyme B500, Polarzyme, Protease M "Amano" G, Kokulase•P, Actinase AS, Gurindoamiru PR59, Gurindoamiru PR43, Flavorzyme, Prometax, Noboran, VERON W, Protease AL, Magnax MT, Sofutagen M2, Collupulin, Fromase, Meito RENNET, Meito RENNNET SUPER, and Maxiren.

The cellulase that may be used in the present invention to decompose celluloses is not particularly limited. Examples include Cellulase A "Amano" 3, Cellulase T "Amano" 4, β-Glucanase, Spezyme CP, Multifect, Multifect GC Extra, Optiflow RC, Primafast, IndiAge NeutraFlex, Accellerase, Optimash, Optimase CX, Puradax HX, GODO-TCF, GODO-TCL, GODO-TCD-H3, VESSELEX, Softagen•C-1, Super-heat-resistant Cellulase, Cellulizer CL, Cellulizer ACE, Cellulase Nagase, Cellzyme C, Cellulase SS. Cellulase XL-531, Bakezyme concreate, Citrase CL, Bakezyme X-CELL, Varidase TRL, Varidase ANC40, CELLSOFT, Carezyme, Celluzyme, Celluclast, Cellic CTec, Cellulosin AC40, Cellulosin AL, Cellulosin TF, Cellulase "onozuka" 3S, Cellulase Y-NC, PANCELASE br, CellSEB Ts, Sumizyme AC, Sumizyme C, Sucrase C, Enchiron MC, Enchiron MCH, BioHIT, Bio-STAR, Cellulase ES, Finizyme, Ultra-Flo, Viscozyme, Glucanex, Filtrase L, Filtrase NLCL, Filtrase Premium L, Sumizyme BGA, and naringinase.

The dosage form of the composition of the present invention is not particularly limited. Examples include dusts, granules, tablets, syrups, injections, drops, powders, suppositories, suspensions, ointments, etc. The composition of the present invention may be administered either orally or parenterally (e.g. intravenous, intramuscular, subcutaneous, rectal or transdermal). The composition may contain additives such as excipients, disintegrants, binders, lubricants, and colorants. Exemplary excipients include lactose, glucose, corn starch, sorbitol, and microcrystalline cellulose; exemplary disintegrants include starch, sodium alginate, gelatin powder, calcium carbonate, calcium citrate, and dextrin; exemplary binders include dimethylcellulose, poly (vinyl alcohol), poly(vinyl ether), methylcellulose, ethylcellulose, gum arabic, gelatin, hydroxypropylcellulose, and poly(vinyl pyrrolidone); exemplary lubricants include talc, magnesium stearate, poly(ethylene glycol), and hardened vegetable oils.

Depending on its dosage form, the composition of the present invention contains varying amounts of chlorophyll c which typically range from about 0.1 to 100 mg by dry weight in the total composition. In the case of an algal powder or extract that contains chlorophyll c as an active ingredient, its content typically ranges from about 0.1 to 10 wt %, preferably from about 1 to 3 wt %, in the total composition.

The dose of administration is determined as appropriate for individual cases in consideration of various factors such as the age, body weight and sex of the patient, the type of disease, and the severity of symptoms, and the frequency of administration may be once or more than once a day. For instance, the dose of administration may be such that chlorophyll c is ingested in a dry weight ranging from 0.1 to 100 mg; an algal powder or extract that contains chlorophyll c as an active ingredient may be ingested in a dry weight ranging from about 0.1 g to 10 g, preferably from about 1 g to 3 g.

The composition of the present invention may, either on its own or after being added to a processed food, serve as a functional food or beverage that has degranulation suppressing activity, allergy suppressing activity or osteoarthritis suppressing activity. The type of the food or beverage to be produced is not particularly limited if it does not interfere with the degranulation suppressing action, allergy suppressing action or osteoarthritis suppressing action of the active ingredient chlorophyll c.

Examples of the processed food to which the composition of the present invention may be added include: bakery; cereal flour and noodles; processed fishery products; processed agricultural and forestry products; processed animal foods; cow's milk and dairy products; oils and fats, either unprocessed or processed; liquors; beverages; seasonings; prepared frozen foods; retorted foods; instant foods; seasoned dried products such as fish/shell senbei; salt preserved fish roe and other products; tsukudani (fish and other foods boiled in soy sauce) such as kanroni, shigureni, and kakuni; broiled processed products; boiled processed products; seasoned processed products such as fish/shell miso; kamaboko (minced and steamed fish) such as mushi(steamed)-kamaboko, yaki(broiled)-kamoboko, age(fried)-kamaboko, yude (boiled)-kamaboko, fuumi(flavored)-kamaboko, housou (packaged)-kamaboko, saiku(crafted)-kamaboko, and kunsei(smoked)-kamaboko; pickles such as shoyu(soy)-zuke, miso-zuke, kasu(sake lees)-zuke, su(vinegar)-zuke, and koji(rice malt)-zuke; shiokara (salted fish guts) such as katsuo(bonito)-shiokara, uni(sea urchin)-shiokara, and ika (squid)-shiokara; canned products; binned products; fish sauce; and extract products.

The food and beverage of the present invention encompass health foods and beverages, dietary supplements, foods for specified health uses, foods with nutrient functional claims, etc. The "foods for specified health uses" refers to those foods and beverages that are ingested in dietary life for a specified health purpose and which have a label claiming that the specified health purpose may be achieved by ingesting them. Such foods and beverages may have labels attached thereto, claiming that they "alleviate symptoms of allergy," "alleviate symptoms of pollinosis," "alleviate symptoms of atopic dermatitis," "alleviate symptoms of osteoarthritis," or that they are "foods for persons worried about allergy" or "foods for persons worried about osteoarthritis."

The composition of the present invention may, either on its own or after being added to a feed or pet food, serve as a feed or pet food that has degranulation suppressing activity, allergy suppressing activity or osteoarthritis suppressing activity. The type of the feed or pet food to be produced is not particularly limited if it does not interfere with the degranulation suppressing action, allergy suppressing action or osteoarthritis suppressing action of the active ingredient chlorophyll c.

The feed or pet food of the present invention is not particularly limited in scope and they may be feeds for cattle and poultry such as cows, pigs and chickens, or feeds for farming crustaceans and fish/shellfish, or pet foods for companion animals such as dogs, cats, hamsters, and squirrels. The form the feed or pet food of the present invention can take is not particularly limited and examples include a pellet type, a crumble type, a flake type, a bulky type, a dry type, a wet type, a semi-moist type, a biscuit type, a sausage type, a jerky type, a powder type, a granule type, a capsule type, etc.

EXAMPLES

The present invention will be described below more specifically by reference to Examples. It should, however, be understood that the following Examples are by no means intended to limit the scope of the present invention.

(Example 1) Test for Evaluating the Degranulation Suppressing Activity of Chlorophyll c Chlorophylls, heretofore unknown to have a degranulation suppressing action, were subjected to a test as described below for evaluating their degranulation suppressing activity using the rat basophile derived cell line RBL-2H3.

First, the rat basophile derived cell line RBL-2H3 was diluted with a DMEM medium (product of SIGMA) containing 10% fetal bovine serum (hereinafter referred to as FBS) to give a density of $2.5 \times 10^5$ cells/ml, dispensed on a 24-well culture plate in a volume of 1 ml/well, and cultured overnight at 37° C. under conditions of 5% $CO_2$ and 100% humidity. After removing the culture supernatant, the cell surfaces were washed with 1 ml/well of a phosphate buffer solution (hereinafter referred to as PBS) and an anti DNP-IgE solution prepared by diluting mouse monoclonal anti-dinitrophenol (product of SIGMA) with a DMEM medium to give a concentration of 50 ng/ml was added in a volume of 500 µl/well, followed by incubation for 2 hours at 37° C. under conditions of 5% $CO_2$ and 100% humidity. After the end of incubation, the anti DNP-IgE solution was removed and washing was done using 1.5 ml/well of a buffer solution containing 137 mM NaCl (product of nacalai tesque), 2.7 mM KCl (JUNSEI CHEMICAL), 1.8 Mm $CaCl_2.2H_2O$ (JUNSEI CHEMICAL), 1 mM $MgCl_2. 6H_2O$ (JUNSEI CHEMICAL), 5.6 mM glucose (Wako Pure Chemical Industries), 20 mM HEPES (Wako Pure Chemical Industries) and 0.1% BSA (the buffer solution being a modified Tyrode buffer which is hereinafter referred to as "MT buffer"); this procedure was repeated twice. Next, an MT buffer containing 0.5% of a chlorophyll, i.e., an authentic sample of chlorophyll a (product of DHI), an authentic sample of chlorophyll b (product of DHI), an authentic sample of chlorophyll c2 (product of DHI), or an authentic sample of chlorophyll d (purified from cyanobacteria adhering to surfaces of red algae, by referring to Non-Patent Documents 10 and 11, for example) was added in a volume of 490 µl/well and incubation was conducted for 10 minutes at 37° C. under conditions of 5% $CO_2$ and 100% humidity. To a control group that would not undergo suppression of the degranulation reaction, an MT buffer containing 0.5% ethanol was added. After 10-min incubation, Albumin, dinitrophenyl (product of SIGMA) was added to give a concentration of 200 ng/ml and the mixture was stirred to homogeneity, followed by 30-min incubation at 37° C. under conditions of 5% $CO_2$ and 100% humidity. After the end of incubation, the mixture was ice-cooled for 10 minutes to quench the reaction and 500 μl of the supernatant was recovered. To the cells from which the culture supernatant was recovered, Cell Lysate buffer (product of SIGMA) was added in a volume of 500 μl/well and thereafter an ultrasonic cell disrupter was used to form a homogeneous cell lysate which was recovered in a volume of 500 μl. The culture supernatant and the cell lysate were dispensed on a 96-well plate, each in a volume of 50 μl/well, and incubated at 37° C. for 5 minutes. After the end of incubation, an aqueous solution containing 100 mM citric acid and 3.3 mM p-nitrophenyl-2-acetoamido-2-deoxy-β-D-glucopyranoside (product of Wako Pure Chemical Industries) (the aqueous solution is hereinafter referred to as a "substrate solution") was added in a volume of 100 μl/well and after thorough mixing, incubation was conducted at 37° C. for 25 minutes. After the end of incubation, an aqueous solution containing 2 M glycine (the aqueous solution is hereinafter referred to as a "reaction quencher") was added in a volume of 100 μl/well and thorough mixing was conducted to quench the reaction; thereafter, a plate reader was used to measure the absorbance at 405 nm. Through this sequence of reactions, degranulation occurred and the activity of β-hexosaminidase contained in the granules was measured to calculate the proportion of granules released from the cells to the culture supernatant. For evaluation, the proportion of granules released into the culture supernatant from the cells in the control group to which 0.5% of 100% ethanol had been added instead of the test sample and which would not undergo suppression of degranulation was taken as 100% and the proportion of granules released from the cells in each test sample added group into the culture supernatant was counted as percent degranulation relative to this reference value.

For efficacy evaluation, a Dunnett multiple comparison test was conducted on those groups that were found to have statistically significant differences by variance analysis. In a graph showing the result, the group found to have a significant difference at a 5% significance level was marked by symbol * whereas the group found to have a significant difference at a 1% significance level was marked by symbol **. The same test was conducted in Example 2 and subsequent Examples.

Figure 1:
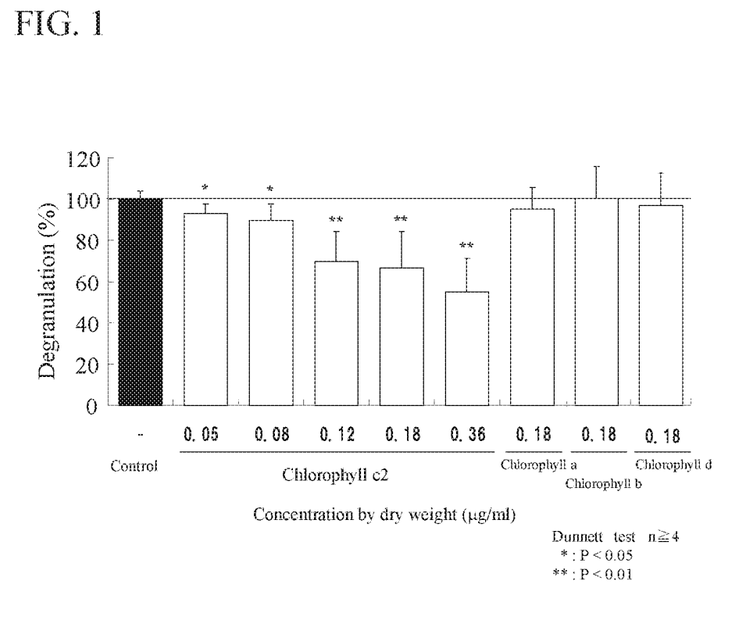
FIG. 1 is a graph showing in terms of percent degranulation the result of a test conducted to evaluate the activity of chlorophyll species a to d for suppressing degranulation of rat basophile derived cell line RBL-2H3.

As shown in FIG. 1, the authentic samples of chlorophyll a, b and d were recognized to have no degranulation suppressing activity at all; on the other hand, the groups treated with the authentic sample of chlorophyll c2 were shown to exhibit the degranulation suppressing activity in a dose-dependent manner which was already apparent when chlorophyll c2 was added in a very low concentration which was only about 0.05 μg/ml by dry weight. It was therefore clear that chlorophyll c2 has a very strong activity for suppressing degranulation which has heretofore been entirely unknown in chlorophylls; the use of chlorophyll c2 has thus been verified to be effective for preventing or treating allergic symptoms as of pollinosis and osteoarthritis, both involving the degranulation reaction.

(Example 2) Test for Evaluating Percent Cell Survival Using Basophile Derived Cell Line RBL-2H3

The rat basophile derived cell line RBL-2H3 diluted to the same concentration as in Example 1 was dispensed on a 96-well culture plate in a volume of 0.1 ml/well and cultured overnight at 37° C. under conditions of 5% $CO_2$ and 100% humidity. After removing the culture supernatant, the cell surfaces were washed with 1 ml/well of PBS and then an MT buffer containing an authentic sample of chlorophyll c2 at the same concentrations by dry weight as in Example 1 was added in a volume of 100 μl/well and incubation was conducted for 40 minutes at 37° C. under conditions of 5% $CO_2$ and 100% humidity. To a control group that would not undergo suppression of the degranulation reaction, an MT buffer containing 0.5% ethanol was added. After 40-min incubation, WST-1 reagent (product of DOJINDO) was added in a volume of 10 μg/ml and the mixture was incubated for 30 minutes at 37° C. under conditions of 5% $CO_2$ and 100% humidity. After the end of incubation, the mixture was left to stand at room temperature for 10 minutes and then the absorbance at 450 nm was measured to evaluate the percent cell survival.

Figure 2:
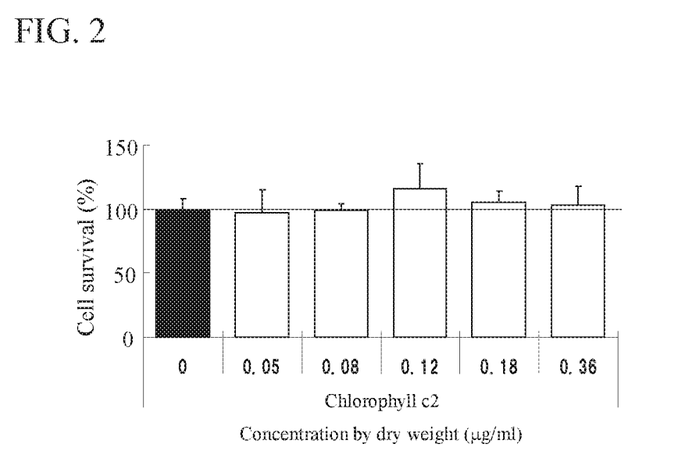
FIG. 2 is a graph showing in terms of percent cell survival the result of a test conducted to evaluate the cytotoxicity of chlorophyll c2 on rat basophile derived cell line RBL-2H3.

The result is shown in FIG. 2; obviously, none of the cell groups treated with the authentic sample of chlorophyll c2 experienced a drop in percent cell survival and it was verified that the degranulation suppressing activity of chlorophyll c2 as demonstrated in Example 1 is not due to cytotoxicity.

(Example 3) Preparation of Chlorophyll c

As noted hereinabove, chlorophyll c is known to be abundant in algae such as those of the Division Dinoflagellata, the Division Cryptophyta, the Division Heterokontophyta including the Class Chrysophyceae, the Class Raphidophyceae, the Class Phaeophyceae, the Class Bacillariophyceae (Diatomea) and the Class Eustigmatophyceae, as well as the Division Haptophyta. Hence, from among chlorophyll c containing algae, hormeri (Turner) C. Agardh which is readily available and which has been part of people's dietary life was particularly selected for the purpose of concentrating chlorophyll c in a convenient and inexpensive way by removing salts, polysaccharides and other non-chlorophyll c water-soluble and water-insoluble impurities; the alga was washed under stirring for 3 minutes using 15 volumes of water and after repeating the same washing operation three times, the alga was dried overnight under the condition of 25° C. and ground with a mill to remove any unwanted matter that was not chlorophyll c, whereby a dry powder of the brown alga hormeri (Turner) C. Agardh was obtained as a concentrated form of chlorophyll c.

For the purpose of concentrating chlorophyll c even further, the thus produced dry powder of the brown alga hormeri (Turner) C. Agardh as a concentrated form of chlorophyll c was subjected to extraction with stirring overnight under the condition of 25° C.; the extraction solvent was water or 20% or 40% or 60% or 80% hydrous ethanol or 100% ethanol, whose volume was 15 times the dry weight of the powder. After the extraction, suction filtration was performed to remove the insoluble matter and the resulting extract was rotary evaporated to dryness.

Figure 3:
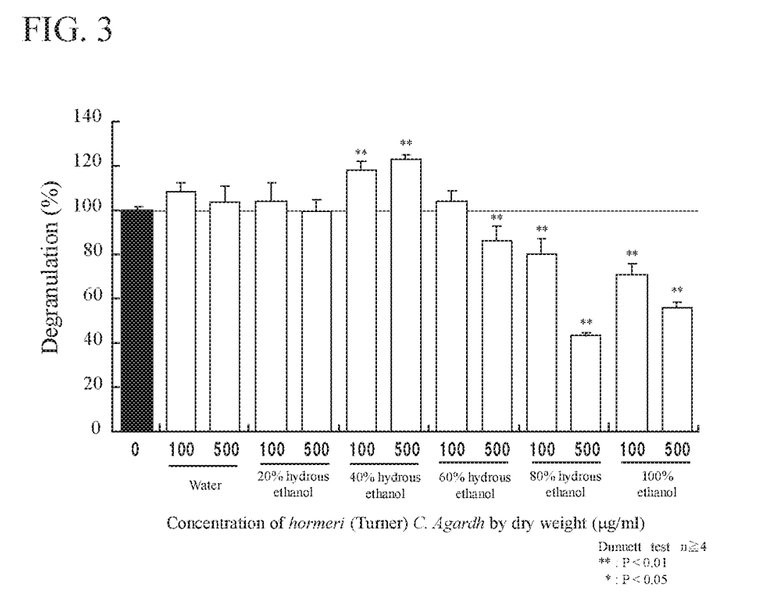
FIG. 3 is a graph showing in terms of percent degranulation the result of a test conducted to evaluate how effectively chlorophyll c as extracted from *hormeri* (Turner) C. Agardh with water, or hydrous ethanol at 20%, 40%, 60% or 80%, or 100% ethanol were able to suppress degranulation of rat basophile derived cell line RBL-2H3.

The extracts thus evaporated to dryness were evaluated for the degranulation suppressing activity using the rat basophile derived cell line RBL-2H3 as in Example 1. The results are shown in FIG. 3; obviously, the extract prepared using water was found to have no degranulation suppressing activity at all and only the extracts prepared using 60-80% hydrous ethanol or 100% ethanol were found to have the activity of interest, which was strongest in the extract prepared using 80% hydrous ethanol. It was therefore verified that using 60-80% hydrous ethanol or 100% ethanol is effective for efficient extraction of chlorophyll c and that chlorophyll c can be extracted most efficiently when 80% hydrous ethanol is used; thus, from the dry powder of the brown alga *hormeri* (Turner) C. Agardh as a concentrated form of chlorophyll c, extracts as a highly concentrated form of chlorophyll c were prepared using hydrous ethanol.

Figure 4:
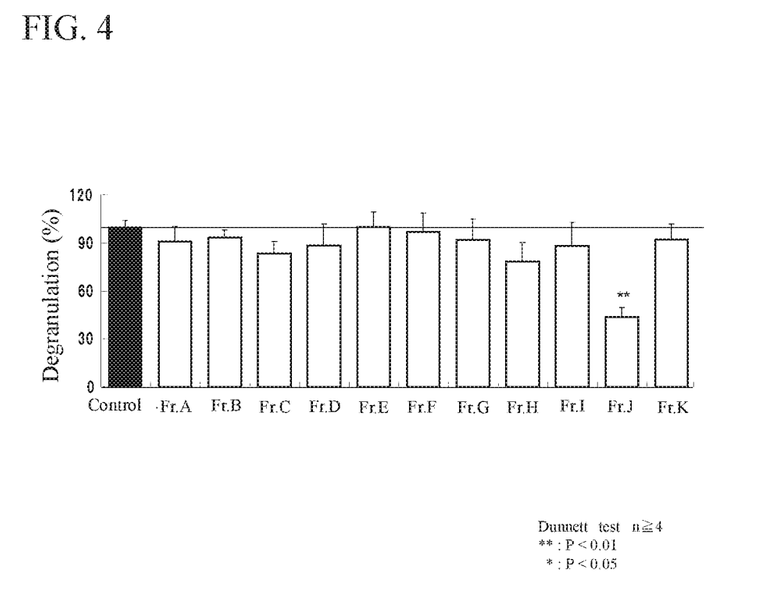
FIG. 4 is a graph showing the percent degranulation of each of the fractions as obtained by HPLC on an extract of *hormeri* (Turner) C. Agardh with an aqueous ethanol solution.
Figure 5:
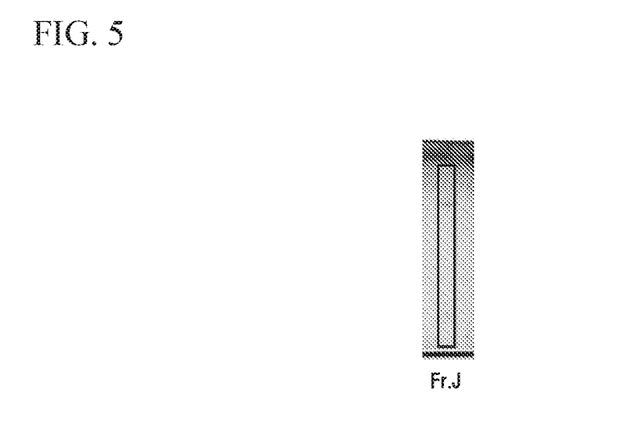
FIG. 5 is a photograph showing a spot of an active fraction (Fr. J in FIG. 4) as observed in thin-layer chromatographic analysis.
Figure 6:
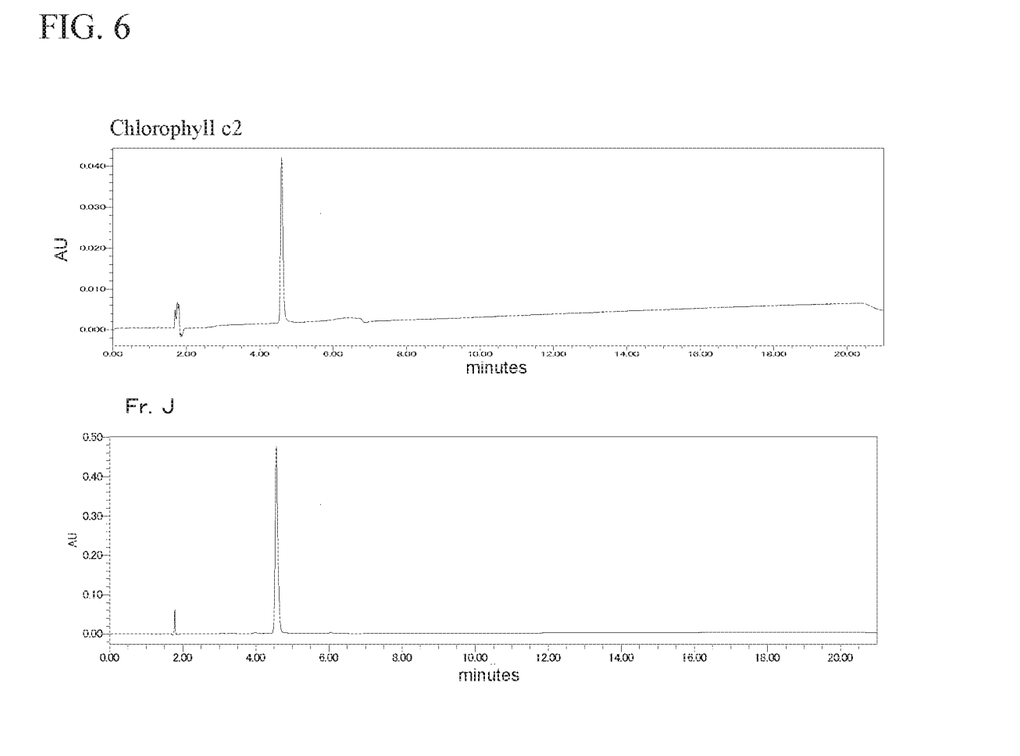
FIG. 6 is a set of charts showing the absorbances at absorption wavelength 450 nm of an active fraction (Fr. J in FIG. 4) as obtained by HPLC and an authentic sample of chlorophyll c2.
Figure 7:
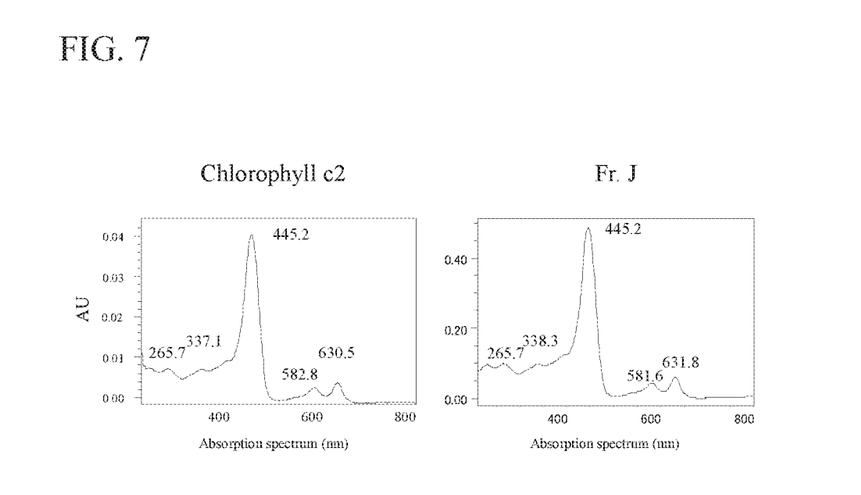
FIG. 7 is a set of charts showing the absorption spectra of an active fraction (Fr. J in FIG. 4) as obtained by HPLC and an authentic sample of chlorophyll c2.

For the purpose of concentrating chlorophyll c still further, the 80% hydrous ethanol extract characterized by most efficient extraction of chlorophyll c from the dry powder of the brown alga *hormeri* (Turner) C. Agardh as a concentrated form of chlorophyll c was subjected to phase separation using n-butanol and water, and the resulting n-butanol fraction was subjected to further phase separation using hexane and 90% hydrous methanol. The resulting 90% hydrous methanol fraction was fractionated on a silica gel column (product of YAMAZEN CORPORATION) and the same fraction procedure was repeated three times. The resulting concentrated fraction of chlorophyll c was loaded on an ODS column (product of Waters), eluted on a gradient using a 45% aqueous acetonitrile solution and 100% acetonitrile, and fractionated by HPLC involving peak identification based on the absorbance at a wavelength of 254 nm to yield eleven fractions A to K. The resulting fractions were subjected to a test for evaluating degranulation suppressing activity using the rat basophile derived cell line RBL-2H3 as in Example 1; the results are shown in FIG. 4 and only Fr. J was found to have the evaluating degranulation suppressing activity. The photo of FIG. 5 verified that the active fraction Fr. J had been purified to a single band; Fr. J and an authentic sample of chlorophyll c2 (product of DHI) were measured for the absorbance at 450 nm by HPLC; as FIG. 6 shows, Fr. J and the authentic sample of chlorophyll c2 were found to have the same peak at a retention time of about 4.6 minutes; in addition, as FIG. 7 shows, Fr. J and the authentic sample of chlorophyll c2, both dissolved in an aqueous acetonitrile solution, had an identical absorption spectrum; with these results taken together, Fr. J was identified as chlorophyll c2; thus, the 80% hydrous ethanol extract of chlorophyll c from the dry powder of the brown alga *hormeri* (Turner) C. Agardh as a concentrated form of chlorophyll c could be processed by the sequence of those operations to prepare an even mroe purified form of chlorophyll c2.

(Example 4) Test for Evaluating Degranulation Suppressing Activity of Chlorophyll c1 or c3

Figure 8:
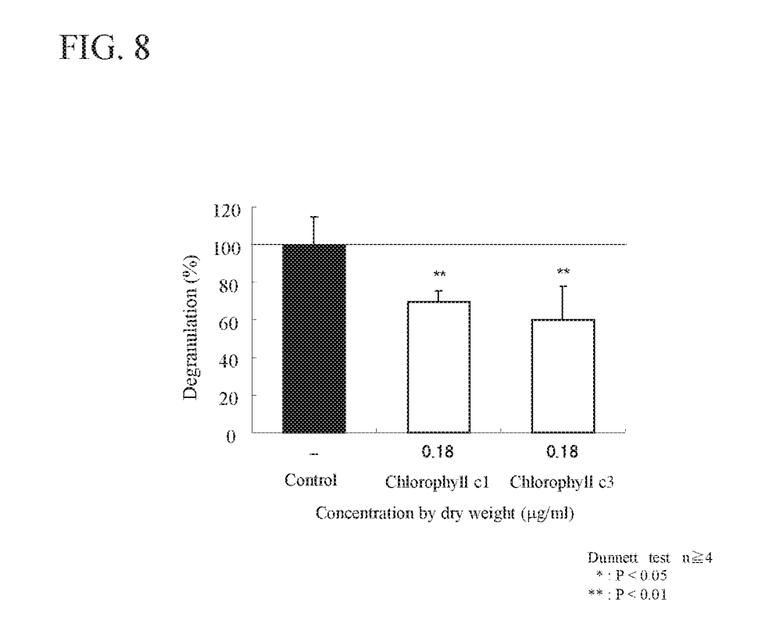
FIG. 8 is a graph showing in terms of percent degranulation the result of a test conducted to evaluate the activity of chlorophyll c1 or c3 for suppressing degranulation of rat basophile derived cell line RBL-2H3.

Chlorophyll c1 or c3 which had heretofore been entirely unknown to have the degranulation suppressing action were evaluated for the degranulation suppressing activity as in Example 1. The result is shown in FIG. 8; obviously, the groups respectively treated with an authentic sample of chlorophyll c1 (prepared from a brown alga by referring to Non-Patent Document 12, for example) or an authentic sample of c3 (product of DHI) were found to exhibit the degranulation suppressing activity as did chlorophyll c2 which was verified to have the same activity in Example 1. It was therefore clear that not only chlorophyll c2 which was verified to be active in Example 1 but also chlorophyll c1 and c3 alike has an activity for suppressing degranulation which has heretofore been entirely unknown in chlorophylls; the use of either type of chlorophyll c was thus verified to be effective for preventing or treating allergic symptoms as of pollinosis and osteoarthritis, both involving the degranulation reaction.

(Example 5) Test for Evaluating Percent Cell Survival Due to Chlorophyll c1 or c3

Figure 9:
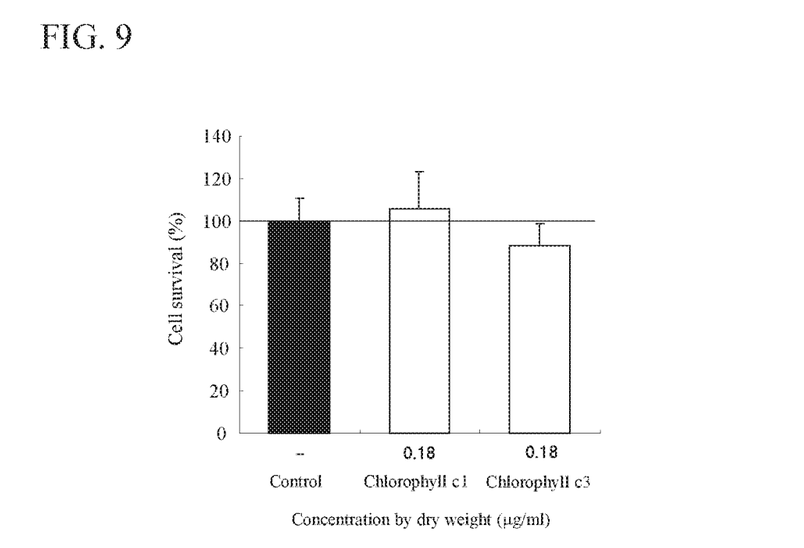
FIG. 9 is a graph showing in terms of percent cell survival the result of a test conducted to evaluate the cytotoxicity of chlorophyll c1 or c3 on rat basophile derived cell line RBL-2H3.

Chlorophyll c1 and c3 were subjected to a test for evaluating the percent cell survival using the rat basophile derived cell line RBL-2H3 as in Example 2. The result is shown in FIG. 9; obviously, neither the cell group treated with the authentic sample of chlorophyll c1 nor the cell group treated with the authentic sample of chlorophyll c3 was recognized to experience a drop in the percent cell survival the groups, verifying that the degranulation suppressing activity of chlorophyll c1 or c3 which was demonstrated in Example 4 is not due to cytotoxicity.

Figure 10:
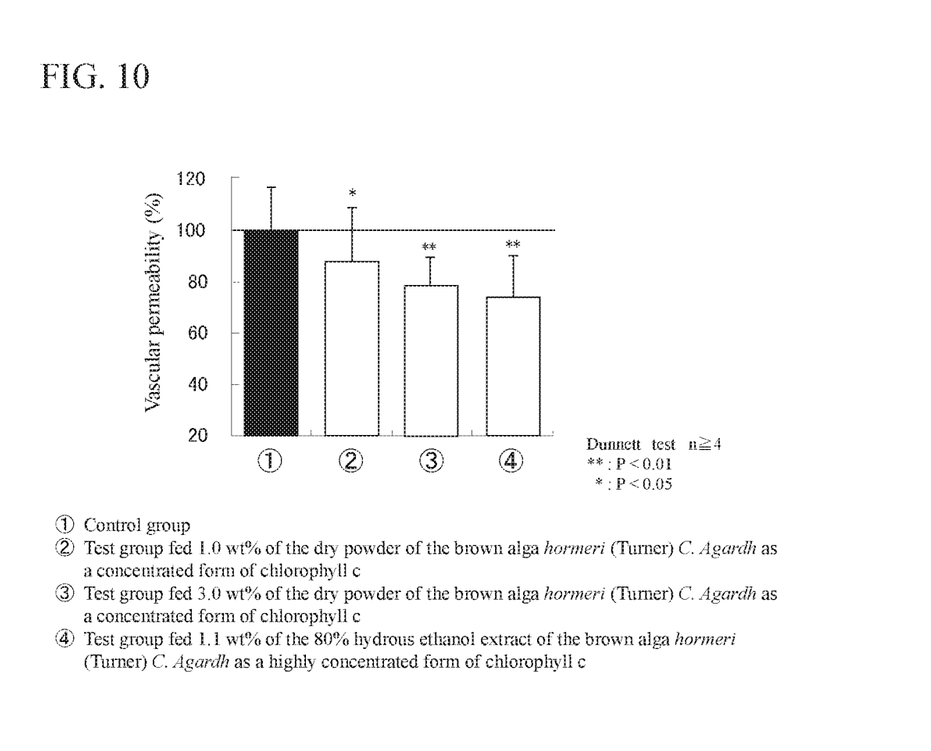
FIG. 10 is a graph showing the percent vascular permeability of SD rat groups that were subjected to a test for evaluating the vascular permeation suppressing activity of a feed supplemented with chlorophyll c as extracted from *hormeri* (Turner) C. Agardh.

(Example 6) Test for Evaluating Vascular Permeability Suppressing Activity Using SD Rat To five-week-old SD male rats acclimatized for a week, a feed consisting of documented formula blend AIN-76 (product of Oriental Yeast) and 3 wt % or 1 wt % of the dry powder of the brown alga *hormeri* (Turner) C. Agardh as a concentrated form of chlorophyll c which was prepared in Example 3 was given ad libitum for 28 days. To another group of similarly acclimatized five-week-old SD male rats, a feed consisting of documented formula blend AIN-76 and 1.1 wt % of the 80% hydrous ethanol extract of the brown alga *hormeri* (Turner) C. Agardh which was also prepared in Example 3 was given ad libitum for 28 days. To a control group, only documented formula blend AIN-76 was given ad libitum for 28 days. Each of these SD male rats which were given the respective feeds ad libitum for 28 days was injected with Evans blue dye into the tail vein. The animals were then injected intradermally at the back with Compound 48/80, a drug for invoking degranulation-mediated vascular permeation. After cervical dislocation under anesthesia, the dorsal skin of each animal was peeled and the amount of Evans blue dye penetrating the peeled skin tissue was quantified by measuring the absorbance at 620 nm with a plate reader. From the quantified amounts of Evans blue dye, the percent vascular permeability was calculated as the relative amount of Evans blue dye penetrating the subcutaneous tissue of each SD male rat on test feed, with the amount of Evans blue dye penetrating the subcutaneous tissue of each SD male rat in the control group being taken as 100%. The results are shown in FIG. 10; obviously, the groups to which the feeds containing 1 wt % or 3 wt % of the dry powder of the brown alga *hormeri* (Turner) C. Agardh as a concentrated form of chlorophyll c were given ad libitum for 28 days, as well as the group to which the feed containing 1.1 wt % of the extract of the brown alga *hormeri* (Turner) C. Agardh was given ad libitum for 28 days were suppressed in vascular permeation as compared with the control group. It was therefore clear that in the in vivo test, too, oral ingestion of the dry powder of the brown alga *hormeri* (Turner) C. Agardh as a concentrated form of chlorophyll c or the 80% hydrous ethanol extract of the brown alga *hormeri* (Turner) C. Agardh, both being prepared in Example 3, were able to suppress degranulation-mediated vascular permeation, thus proving effective for preventing or treating allergic diseases such as pollinosis in which vascular permeation is involved.

Figure 11:
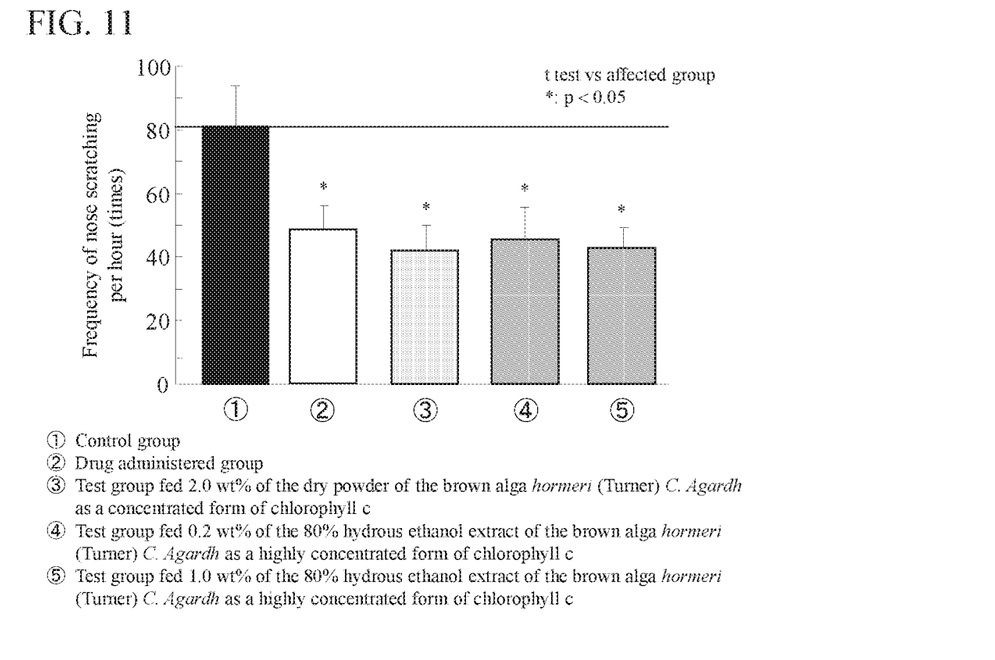
FIG. 11 is a graph showing the number of nose scratches per hour by C57BL/6 mice that were subjected to a test for evaluating the pollinosis suppressing activity of a feed supplemented with chlorophyll c as extracted from *hormeri* (Turner) C. Agardh.

(Example 7) Test for Evaluating Pollinosis
Suppressing Activity Using C57BL/6 Mouse Four-week-old C57BL/6 male mice (product of Charles River Laboratories Japan) were acclimatized for a week. To a group of these animals, 2 g/kg of the dry powder of the brown alga *hormeri* (Turner) C. Agardh as a concentrated form of chlorophyll c which was prepared in Example 3 was orally administered in a repeased-dose and forced manner for 4 weeks as suspended in a 0.5% CMC solution. To another group of the animals, 0.2 g/kg or 1 g/kg of the 80% hydrous ethanol extract of an even more concentrated form of chlorophyll c from the brown alga *hormeri* (Turner) C. Agardh which was also prepared in Example 3 was orally administered in the same manner for 4 weeks as suspended in a 0.5% CMC solution. To a control group, only a 0.5% CMC solution was orally administered in the same manner for 4 weeks. To yet another group of the animals (drug administered group), Olopatadine (product of SIMGA), a pharmaceutical showing a pollinosis suppressing effect by the degranulation suppressing action, was orally administered in the same manner for 4 weeks as suspended in a 0.5% CMC solution. After the 4-week oral administration in a repeased-dose and forced manner, a solution having anti-DNP-IgE dissolved in physiological saline at a concentration of 50 μg/ml was injected into the hip vein of each mouse for passive sensitization. Five days after the sensitization, DNP-OVA antigen as dissolved in physiological saline at a concentration of 50 mg/ml was administered into both nostrils of each mouse to invoke a rhinitic symptom and the symptom of the developed pollinosis was evaluated by counting how many times each rat scratched its nose per hour on account of the pollinosis symptom. The results are shown in FIG. 11; obviously, the group that ingested 2 g/kg of the dry powder of the brown alga *hormeri* (Turner) C. Agardh as a concentrated form of chlorophyll c which was prepared in Example 3, as well as the group that ingested 1 g/kg or 0.2 g/kg of the 80% hydrous ethanol extract of an even more concentrated form of chlorophyll c from the brown alga *hormeri* (Turner) C. Agardh which was also prepared in Example 3, scratched their nose less frequently than the control group, and both the dry powder and the extract were comparable in potency to the drug Olopatadine. It was therefore clear that oral ingestion of the dry powder of the brown alga *hormeri* (Turner) C. Agardh as a concentrated form of chlorophyll c or the 80% hydrous ethanol extract of the brown alga *hormeri* (Turner) C. Agardh, both being prepared in Example 3, were able to suppress vascular permeation which was verified in Example 6 to result from the degranulation reaction, thereby suppressing the symptom of pollinosis to prove effective for preventing or treating allergic rhinitis such as pollinosis.

Figure 12:
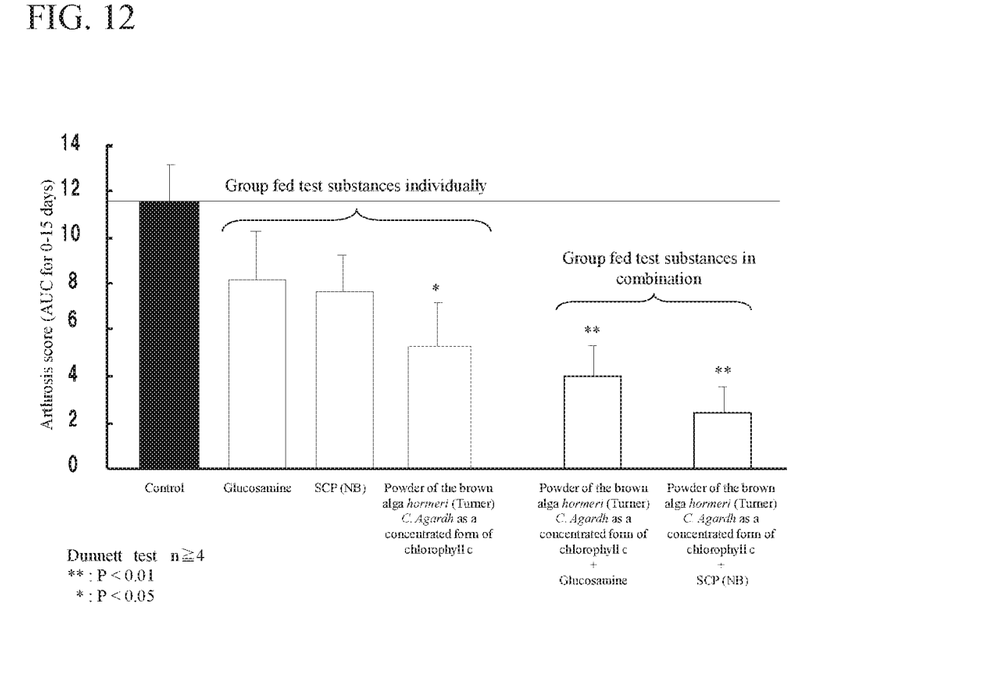
FIG. 12 is a graph showing the result of a test performed on DA rats to evaluate the osteoarthritis suppressing activity after they were given a feed supplemented with chlorophyll c as extracted from *hormeri* (Turner) C. Agardh, a feed supplemented with glucosamine, a feed supplemented with SCP (NB), a feed supplemented with a chlorophyll c extract and glucosamine, and a feed supplemented with a chlorophyll c extract and SCP (NB); the data represent the sum of arthritis scores from the day of onset of the disease (day 0) up to the 15$^{th}$ day of onset.

(Example 8) Test for Evaluating Type II Collagen
Sensitized Osteoarthritis Suppressing Activity
Using DA Rat Six groups of eight-week-old DA/Slc female rats (product of SANKYO LABO SERVICE CORPORATION) that had been acclimatized for a week were allowed to ingest ad libitum the following feeds, respectively, for 4 weeks: a feed consisting of formula blend CRF-1 (product of Oriental Yeast) and 3 wt % of the dry powder of the brown alga *hormeri* (Turner) C. Agardh as a concentrated form of chlorophyll c which was prepared in Example 3; a feed consisting of formula blend CRF-1 and 2 wt % of glucosamine (product of Yaizu Suisankagaku Industry); a feed consisting of formula blend CRF-1 and 5 wt % of edible chondroitin sulfate (designated as SCP(NB); product of Maruha Nichiro Foods); a feed consisting of formula blend CRF-1 and 3 wt % of the dry powder of the brown alga *hormeri* (Turner) C. Agardh as a concentrated form of chlorophyll c which was prepared in Example 3 plus 2 wt % of glucosamine; a feed consisting of formula blend CRF-1 and 3 wt % of the dry powder of the brown alga *hormeri* (Turner) C. Agardh as a concentrated form of chlorophyll c which was prepared in Example 3 plus 5 wt % of SCP(NB); and formula blend CRF-1 only (control group). After the four-week ingestion ad libitum, bovine type II collagen in solution (product of Collagen Gijutsu Kenshukai) which was an arthrosis invoking substance was injected intradermally at four sites of the lumbar portion of the back at a dose of 0.15 mg to thereby invoke osteoarthritis. Thereafter, each animal was visually checked for the state of the footpad of its right and left hind paw and the developed arthrosis was evaluated by scoring against the criteria listed in Table 1 below. The results are shown in FIG. 12; obviously, the rats that were allowed to ingest ad libitum the feed consisting of formula blend CRF-1 and 3 wt % of the dry powder of the brown alga *hormeri* (Turner) C. Agardh as a concentrated form of chlorophyll c which was prepared in Example 3 had lower arthrosis scores than the rats of the control group. It was also shown that the effectiveness of this feed was quite potent and more than comparable to that observed in the group that was allowed to ingest ad libitum the feeds consisting of formula blend CRF-1 and glucosamine or SCP(NB) which are conventionially used to prevent or treat osteoarthritis. Moreover, the dry powder of the brown alga *hormeri* (Turner) C. Agardh as a concentrated form of chlorophyll c which was prepared in Example 3 was verified to be more potent in suppressing osteoarthritis when it was ingested together with glucosamine or SCP(NB) than when the feed consisting of formula blend CRF-1 and glucosamine or SCP(NB) only was ingested ad libitum. From these results, it became clear that osteoarthritis can be suppressed by ingesting the dry powder of the brown alga *hormeri* (Turner) C. Agardh as a concentrated form of chlorophyll c which was prepared in Example 3. It also became clear that a more potent osteoarthritis suppressing action is exhibited by using the conventional osteoarthritis suppressor glucosamine or SCP(NB) in combination with the dry powder of the brown alga *hormeri* (Turner) C. Agardh as a concentrated form of chlorophyll c which was prepared in Example 3.

TABLE 1

| Score | State of the footpad of the hind paw |
|---|---|
| 0 | Normal |
| 1 | Reddened |
| 2 | Redness and slight edema on toes |
| 3 | Edema spread from toes to the entire paw |
| 4 | Intense edema |
| 5 | Joint deformed |

The invention claimed is:
1. A method for alleviating or treating osteoarthritis in a subject, comprising:
   administering to the subject a degranulation suppressor composition comprising an effective amount of chlorophyll c and a pharmaceutically acceptable additive.
2. The method of claim 1, wherein the degranulation suppressor composition further contains glucosamine and/or chondroitin sulfate.

3. The method of claim 1, wherein the composition comprises an algal powder or an algal extract, said algal powder or algal extract having said chlorophyll c.

4. The method of claim 1, wherein the amount of chlorophyll c ranges from about 0.1 to 10 wt % in the total composition.

* * * * *